United States Patent [19]
Feigen et al.

[11] Patent Number: 6,150,114
[45] Date of Patent: *Nov. 21, 2000

[54] METHOD AND REAGENT FOR MONITORING BLOOD LEVELS OF ANTIPLANTELET COMPOUNDS

[75] Inventors: Larry P. Feigen, Wauconda, Ill.; Christopher P. Carron, Wildwood, Mo.; Neal F. Haas, Chicago, Ill.; Debra M. Meyer, Wentzville, Mo.; Jimmy D. Page, Gurnee, Ill.; Jodi A. Pegg, Ballwin, Mo.

[73] Assignee: G. D. Searle & Co., Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/856,761

[22] Filed: May 15, 1997

Related U.S. Application Data

[60] Provisional application No. 60/017,710, May 15, 1996.

[51] Int. Cl.⁷ .................. G01N 33/53; G01N 33/567; C12Q 1/56; C12P 21/06
[52] U.S. Cl. .................. 435/7.1; 435/7.1; 435/7.21; 435/13; 435/69.1; 435/334; 435/337; 435/808; 435/975; 530/388.22; 530/388.25
[58] Field of Search ..................... 435/7.1, 7.21, 435/13, 975, 69, 808, 334, 337; 530/388.22, 388.25

[56] References Cited

U.S. PATENT DOCUMENTS

| | | |
|---|---|---|
| 4,393,040 | 7/1983 | Lopapa et al. . |
| 4,871,677 | 10/1989 | Baugh et al. . |
| 5,182,260 | 1/1993 | Maraganore et al. ............... 514/12 |
| 5,344,957 | 9/1994 | Bovy et al. . |
| 5,662,671 | 9/1997 | Barbut et al. . |

FOREIGN PATENT DOCUMENTS

| | | |
|---|---|---|
| 0520436A2 | 12/1992 | European Pat. Off. . |
| WO9422820 | 10/1994 | WIPO . |

OTHER PUBLICATIONS

Ammar et al., Circulation, 95(3):614–617, Feb. 4, 1997.

Salyers et al., Thrombosis Research, 75(4):409–417, 1994.

Moliterno, et al., American Journal of Cardiology, vol. 75, No. 8, pp. 559–562 (1995).

*Primary Examiner*—James C. Housel
*Assistant Examiner*—Ja-Na Amira Hines

[57] ABSTRACT

A method for determining the amount of an antiplatelet compound in a subject being treated with the compound which comprises calculating the ACT number of the subject's blood containing a reagent which immunoreacts with the antiplatelet compound and comparing the figure to a standardized concentration figure. In subjects concurrently being treated with heparin and antiplatelet compounds, the method can be practiced without additional heparin added to the blood sample. The invention also provides reagents which immunoreact with antiplatelet compounds and kits comprising immunoreactive reagents.

28 Claims, 5 Drawing Sheets

METHOD AND REAGENT FOR MONITORING BLOOD LEVELS OF ANTIPLANTELET COMPOUNDS

This application claims priority under 35 USC § 119(e) of United States provisional application Serial No. 60/017,710 filed May 15, 1996.

BACKGROUND OF THE INVENTION

1. Field of the Invention

This invention generally relates to methods for monitoring the amount of antiplatelet compounds administered to a subject. More particularly, the invention provides methods and kits which allow for the rapid determination of the amount of an antiplatelet compound in a subject by the measurement of the activated clotting time of the subject's blood.

2. Description of the Prior Art

Platelets have a beneficial function in the cessation of blood flow (hemostasis) by providing the initial hemostatic plug at sites of vascular injury. Generally, the platelet first adheres to macromolecules in the subendothelial regions of an injured blood vessel and then aggregates to form the primary hemostatic plug. The aggregate of platelets near the injury then activates plasma coagulation factors which lead to the formation of a fibrin clot that supports and reinforces the aggregate.

Platelets also participate in harmful reactions such as those leading to atherosclerosis and pathological thrombosis. Thrombosis is a process in which a platelet aggregate and/or fibrin clot blocks a blood vessel. A thrombus blocking an artery may lead to the death of the tissue which is supplied blood by that artery. This blockage causes such conditions as stroke, unstable angina and myocardial infarction. Thrombosis can also cause complications after surgical procedures. For example, blood clots can form at sites which have been opened for implantation of prostheses, such as artificial heart valves, or for percutaneous transluminal angioplasty (PCTA). Antagonists of platelet function have therefore been studied and antiplatelet compounds developed to treat or prevent such complications arising from atherosclerosis and pathological thrombosis.

Many antiplatelet compounds having different functions are described in the art. Zablocki et al. describe fibrinogen receptor antagonists in development which function by disrupting the fibrinogen-platelet glycoprotein IIb/IIIa ("gpIIb/IIIa") interaction and are active inhibitors of all platelet activating agents. Zablocki, J. A. et al., *Exp. Opin. Invest. Drugs*, (1994) Vol. 3(5), pp. 437–448. Compounds such as dipyridamole, ticlopidine and aspirin are also known antiplatelet compounds. Majerus, P. W. et al. in *Goodman and Gilman's The Pharmacological Basis of Therapeutics* (Hardman, J. and Limbird, L. 9th Ed. 1996) pp. 1341–1359. Several patents covering antiplatelet compounds have issued and applications for patents covering additional compounds have been published. For example, U.S. Pat. No. 5,344,957 (Bovy et al.) discloses substituted β-amino acid derivatives useful as platelet aggregation inhibitors and PCT Application Publication No. WO 94/22820 (Abood et al.) discloses 1-amidinophenyl-pyrrolidones, piperidinones and azetinones useful as platelet inhibitors. The disclosures of these references, patents and publications, including the references cited therein, are hereby incorporated into this specification to more fully define the state of the art.

Measurement of activated clotting times was developed by Hattersly as a sensitive test to monitor whole blood clotting. Hattersly, P. G., *J.A.M.A.*, (1966) Vol. 196, pp. 150–154. Others have used the test as an assay to demonstrate drug activity. Moliterno et al. describe the increase of activated clotting times when the anti-gpIIb/IIIa antibody C7E3 is administered. Moliterno, D. et al. *Am. J. Cardiol.*, (1995) Vol. 75, pp. 559–562.

As therapy using antiplatelet compounds increases, methods of monitoring the amount of the compound in the subject being treated becomes increasingly important. Monitoring concentrations, and adjusting doses in response thereto, will prevent overdosing and assist in tracking whether clearance of the compound may be impaired. Thus, a method which allows for a rapid and easy determination of the blood concentrations of these compounds is needed.

We have discovered that antibodies which immunoreact with an antiplatelet compound will affect the activated clotting time or platelet aggregation of blood containing that compound. The activated clotting time has been found to be significantly different in the presence of antibody such that an activated clotting time number, referenced herein as the "ACT number," can be calculated and correlated to a plotted curve or table giving specific concentrations of the compound in the blood, thus providing a rapid, non-labor intensive method of monitoring the concentration of these compounds.

SUMMARY OF THE INVENTION

This invention provides a method for determining the amount of an antiplatelet compound in the blood of a subject being treated with the compound which comprises calculating the ACT number of the subject's blood containing a reagent which immunoreacts with the antiplatelet compound and comparing the calculated ACT number to a standardized concentration curve thereby determining the amount of antiplatelet compound in the blood of the subject.

This invention also provides a method for determining the amount of an antiplatelet compound in a subject being treated with the compound which comprises calculating the ACT number of the subject's blood containing heparin and a reagent which immunoreacts with the antiplatelet compound and comparing the calculated ACT number to a standardized concentration curve thereby determining the amount of antiplatelet compound in the blood of the subject.

This invention also provides a method for determining the concentration of an antiplatelet compound in the blood of a subject being treated with the compound which comprises:

a) taking a blood sample from the subject;

b) separating the sample into at least two portions and adding a reagent which immunoreacts with the antiplatelet compound to at least one of the portions;

c) measuring the activated clotting time of at least one portion of the blood sample from (b) which does not contain the reagent;

d) measuring the activated clotting time of at least one portion of the blood sample from (b) which contains the reagent;

e) calculating the ACT number from the measurements from (c) and (d); and f) comparing the ACT number from (e) to a standardized concentration curve thereby determining the concentration of the antiplatelet compound in the blood of the subject.

This invention further provides a monoclonal antibody produced by a murine hybridoma cell line which immunoreacts with an antiplatelet compound and essentially does not immunoreact with heparin.

Finally, this invention provides a kit for monitoring the concentration of an antiplatelet compound in a subject being treated with the compound comprising a reagent which immunoreacts with the compound.

DETAILED DESCRIPTION OF THE INVENTION

A. Methods

This invention provides a method for determining the amount of an antiplatelet compound in the blood of a subject being treated with the compound which comprises calculating the ACT number of the subject's blood containing a reagent which immunoreacts with the antiplatelet compound and comparing the calculated ACT number to a standardized concentration curve thereby determining the amount of antiplatelet compound in the blood of the subject.

As used herein, "calculating the ACT number" is intended to encompass any calculation which would provide a number which can be compared to a standardized curve. For example, the ACT number may represent the ratio of a) the activated clotting time of the subject's blood sample with the immunoreactive reagent present in the blood sample to b) the activated clotting time of the subject's blood sample without the immunoactive reagent in the blood. Alternatively, the calculated ACT number may represent the difference between the activated clotting times with and without the immunoreactive reagent present in the blood sample. Those skilled in the art will readily recognize other ways of calculating which would not depart from the scope of this invention. In any event, it is anticipated that the ACT number will be calculated in the same manner for the subject's blood sample as the standardized concentration curve so that they can be quickly compared and the concentration of the compound in the blood determined.

As used herein, the phrase "standardized concentration curve" refers to any method of demonstrating the relationship between activated clotting times and blood concentrations of antiplatelet compounds. For example, a standardized concentration curve may have the activated clotting times plotted along the y-axis for an anti-platelet compound and the concentration of the compound plotted along the x-axis. When a number of activated clotting times had been calculated for known concentrations of antiplatelet compounds the plot would most likely be a "curve" as the term is understood by those skilled in the art. Thus, the "comparison" of the calculated ACT number to the standardized curve in this example would comprise finding the value on the y-axis equal to the calculated ACT number and then finding the point on the "curve" which has the same y-axis value and reading the x-axis value for the point on the curve. The x-axis value thus gives the concentration of the compound in the blood.

In another preferred embodiment the "curve" can also be represented by a table of calculated values. Thus, instead of comparing values on x and y axes, these values would be pre-calculated for various ranges and presented in a table which could be read quickly to give a precise value or range for the concentration of the compound in the blood of the subject.

In a separate embodiment the standardized curve could also be represented by a mathematical equation which could then be used to calculate concentration values based on measured activated clotting times. For example this equation, or algorithm, could be incorporated into a computer program which would automatically calculate blood concentrations based on inputted activated clotting times or ACT numbers. Such a program could also be incorporated into the instruments used to measure activated clotting times.

The methods of this invention are preferably used to monitor the concentration of antiplatelet compounds such as gpIIb/IIIa antagonists in the blood of a subject. The subject is preferably a mammal and, more preferably, a human patient undergoing treatment for such ailments as stroke, myocardial infarction, or unstable angina whether as an admitted patient to a hospital or as an ambulatory "outpatient". The methods can also be used to monitor blood levels of antiplatelet compounds in subjects who are undergoing operations to insert prostheses such as artificial heart valves or PCTA.

As noted above, several antiplatelet compounds are being developed and some are undergoing clinical testing. Examples of compounds which could be monitored by the methods of this invention include, but are not limited to, antibody C7E3 (Centocor); MK383: N(butylsulfonyl)-0-(4-(4-piperidinyl)butyl)-L-tyrosine, monohydrochloride (Merck, West Point, Pa., USA 19486-0004); L-703014: (R)-beta[[[[ 1-oxo-4(4-piperidinyl)butyl]amino]acetyl] amino]-1H-indole-3-pentanoic acid (Merck); RO 44-9883: (S)-[[1-[2-[[4-(aminoiminomethyl)benzoyl]amino]-3-(4-hydroxyphenyl)-1-oxopropyl]-4-piperidinyl]oxy]acetic acid (Hoffman LaRoche Nutley, N.J., USA 07110-1199); GR 144.053: 4(4-(4-(aminoiminomethyl)phenyl)-1-piperazinyl)-3-methyl-1-piperidine acetate (Glaxo, Research Triangle Park, N.C., U.S.A. 27709); BIBU 104: methyl trans-5-(S)-[[4-[4-(imino[(methoxycarbonyl)amino] methyl]phenyl]phenoxy]methyl]-2-oxopyrrolidine-3-acetate (Boehringer Ingleheim, Ridgefield, Conn., U.S.A. 06877-0368); DMP 728: N-[3-(aminomethyl)benzoyl]-D-2-aminobutanoyl-N2-methyl-L-arginyl-glycyl-L-aspartic acid, cyclic (41→1)-peptide; (DuPont Merck, Wilmington, Del., U.S.A. 19805 and the cyclic heptapeptide Integrelin™ (COR Therapeutics, So. San Francisco, Calif., USA).

In a preferred embodiment of this method the gpIIb/IIIa antagonist is any of the β-amino acid derivatives described in U.S. Pat. No. 5,344,957, incorporated herein by reference. These derivatives have the general formula:

Particularly preferred embodiments of these derivatives include "compound A" having the structure:

(ethyl 3S-[[4-[[4-(aminoiminomethyl)phenyl]amino]-1,4-dioxobutyl]amino]-4-pentynoate, monohydrochloride).

Compound A is the prodrug form of the active gpIIb/IIIa antagonist "compound B" which has the structure:

(3S-[[4-[[4-(aminoiminomethyl)phenyl]amino]-1,4-dioxobutyl]amino]-4-pentynoic acid).

In another preferred embodiment of these methods the antiplatelet compound is any of the 1-amidinophenyl-pyrrolidones, piperidinones or azetinones described in PCT Application Publication No. WO 94/22820, incorporated herein by reference. These compounds have the general formula:

A particularly preferred embodiment of these compounds is "compound C" having the structure:

(N-[[[1-[4-(aminoiminomethyl)phenyl]-2-oxo-3S-pyrrolidinyl]amino]carbonyl]β-alanine,ethyl ester).

Compound C is the prodrug form of the active gpIIb/IIIa antagonist "compound D" which has the structure:

(3-[[[[1-[4-(aminoiminomethyl)phenyl]-2-oxo-pyrrolidin-3S-yl]amino]carbonyl]amino]propanoic acid, trifluoroacetate).

At the present time, the most widely used compound to prevent clotting of blood in such patients is the anticoagulant heparin. Heparin is a glycosaminoglycan which is found in human tissues that contain mast cells. The heparin administered to subjects is typically extracted from porcine intestinal mucosa or bovine lung. Thus, the methods of this invention can be used on subjects being treated with an antiplatelet compound, such as those described above, either by itself, in combination with other antiplatelet compounds, or in combination with heparin. When the subject is being treated with an antiplatelet compound without heparin, the invention contemplates adding heparin to the sample prior to the measurement of the activated clotting times so as to enhance the effect of the antiplatelet compound.

Thus, the invention also provides a method for determining the amount of an antiplatelet compound in the blood of a subject being treated with the compound which comprises calculating the ACT number of the subject's blood containing heparin and a reagent which immunoreacts with the antiplatelet compound and comparing the calculated ACT number to a standardized concentration curve thereby determining the amount of antiplatelet compound in the blood of the subject.

The invention also provides a method for determining the concentration of an antiplatelet compound in the blood of a subject being treated with the compound which comprises:
  a) taking a blood sample from the subject;
  b) separating the sample into at least two portions and adding a reagent which immunoreacts with the antiplatelet compound to at least one of the portions;
  c) measuring the activated clotting time of at least one portion of the blood sample from (b) which does not contain the reagent;
  d) measuring the activated clotting time of at least one portion of the blood sample from (b) which contains the reagent;
  e) calculating the ACT number from the measurements from (c) and (d); and f) comparing the figure from (e) to a standardized concentration curve thereby determining the concentration of the antiplatelet compound in the subject.

In the practice of the methods of the invention, blood can be drawn from a subject being treated with an antiplatelet compound into a syringe containing heparin or heparin can be added after drawing the blood. The heparin to whole blood ratio should be less than or equal to about 1:10, such that the final concentration of heparin in the blood is in the range of between 1.0 Units/ml and 3.0 Units/ml, preferably about 1.5 Units/ml.

In the practice of the methods of the invention the amount of immunoreactive reagent that should be used is an amount which is effective to neutralize the action of the antiplatelet compound. Methods of determining the effective amount are known to those skilled in the art. In a preferred embodiment, the effective amount would be an amount which would give a final concentration of immunoreactive reagent in the sample between about 100 nM and 500 nM.

Activated clotting times can be measured by several instruments presently available. The two most widely available instruments are the Hemotech (Metronic, Parker Co. U.S.A. 80134-9061) and the Hemochron (International Techindyne; N.J. U.S.A).

The Hemotech uses a mechanical plunger that is dipped in and out of kaolin-activated blood samples. Coagulation tests are performed using multiple two-channel test cartridges. Each cartridge contains a reagent reservoir and a reaction chamber and is either prewarmed in an external heat block or warmed in the instrument. The blood sample is added to the warmed cartridge.

When the test is initiated the machine automatically empties the kaolin reagent into the reaction chamber and begins raising and lowering a plunger in each chamber at predetermined intervals. The action of the plunger mixes the sample with reagent and tests for clot formation. When a clot forms, the downward motion of the plunger is decreased. The decrease in the fall rate of the plunger is detected by a photo-optic system and the formation of a clot is signaled by the machine. Individual clotting times, or the average and differences for the channels, are displayed on the front of the machine. The Hemochron is a similar device which uses diatomaceous earth instead of kaolin to activate clotting of the blood. The Hemochron measures clot formation by monitoring a magnet as it moves away from the detector.

A comparison of the two instruments has shown that the measurements from each machine cannot be used interchangeably. A. Avendaco and J. Ferguson, *J.A.C.C.* (Mar. 15, 1994) Vol. 23 (4) pp. 907–910. Thus, the standardized concentration curve would also be standardized for available testing equipment.

B. Antibodies

In the practice of any of the above-described methods, the reagent which immunoreacts with the antiplatelet compound can be either polyclonal antisera or a monoclonal antibody. In a preferred embodiment the reagent which immunoreacts with the antiplatelet compound is a monoclonal antibody.

The term "antibody" in its various grammatical forms is used herein to refer to immunoglobulin molecules and immunologically active portions of immunoglobulin molecules, i.e., molecules that contain an antibody combining site or "paratope". "Antibody" as used herein can refer to intact immunoglobulin molecules or any portions of an immunoglobulin molecule that contain the paratope, including those portions known in the art as Fab, Fab', F(ab')2, and F(v).

The term "immunoreact" in its various forms refers to the specific binding between an antigenic determinant-containing molecule and a molecule containing an antibody combining site such as a whole antibody molecule or a portion thereof. The term "antigenic determinant" refers to the actual structural portion of the antigen that is immunologically bound by an antibody combining site. The term is also used interchangeably with "epitope". As used herein, the term "specific binding" in its various forms refers to a non-random binding reaction between a cell surface receptor and a ligand molecule.

Polyclonal antibodies or "antisera" can be produced by injecting an animal, for example a goat, mouse or rabbit, with the compound of interest producing antibodies to the compounds. When the antibody level or "titer" reaches a sufficient level, antibody-containing serum is drawn from the animal. Antibodies which immunoreact with a compound of interest can be separated by techniques known to those skilled in the art such as by affinity chromatography.

Monoclonal antibodies can be produced using known methods such as that described by Kohler and Milstein in *Nature*, Vol. 256; pp. 495–497 (1975), the text of which is incorporated herein by reference. Generally, a mouse is inoculated with an antigen of interest. This stimulates the proliferation of lymphocytes expressing antibodies against the antigen. Lymphocytes are taken from the spleen and fused to myeloma cells by treatment with a polymer such as polyethylene glycol. Hybrid cells are selected by growing in a culture which does not allow for the growth of unfused cells. Individual hybrid cells are further cultured and tested for the presence of antibodies that bind the antigen.

In certain instances the antigen of interest may not stimulate the inoculated animal to produce antibodies. In order to ensure production of monoclonal or polyclonal antibodies, the antigen may be connected to a carrier molecule to produce a compound large enough to stimulate an immune response in the animal. Carrier molecules can comprise a protein, for example bovine serum albumin (BSA) or thyroglobulin. The new compounds, comprising the carrier molecule and antigen of interest, are known as haptens and can be prepared by methods known to tho se skilled in the art.

The following hybridomas, which produce monoclonal antibodies particularly preferred for the practice of the methods of this invention, were deposited with the American Type Culture Collection (ATCC) 10801 University Boulevard, Manassas, Va. 20110-2209, USA on Apr. 12, 1996:

1) P187.4D7.B3.A1 (also referred to herein as "4D7") assigned ATTC Accession No. HB-12081; and
2) P187.9F7.A5.A1 (also referred to herein as "9F7") assigned ATTC Accession No. HB-12082.

The hybridomas were deposited under conditions which assure that access to the hybridoma will be restricted during the pendency of the patent application, and that all restrictions on the availability to the public of the hybridoma as deposited will be irrevocably removed upon the granting of the patent.

Thus, this invention provides an antibody which immunoreacts with any of the antiplatelet compounds described above. The antibodies can be purified or unpurified polyclonal antisera or monoclonal antibodies, including immunoreactive fragments thereof. This invention also provides hybridomas which produce or "secrete" the monoclonal antibodies. In a preferred embodiment, this invention also provides a monoclonal antibody, produced by a murine hybridoma cell line, which immunoreacts with an antiplatelet compound and essentially does not immunoreact with heparin.

C. Kits

It is anticipated that the antibodies of the invention will be provided as part of a "kit" for performing the methods of the invention. The kit would provide an immunoreactive "reagent", i.e., the antibodies defined above, for a specific antiplatelet compound. Typically the kit would also include a standardized curve as defined above to compare the calculated ACT numbers and determine the amount of antiplatelet compound in the blood of the subject. However, these curves could otherwise be made available to the public or could be determined by one skilled in the art using routine skills and the teaching of the subject invention.

Thus, the invention also provides a kit for monitoring the concentration of an antiplatelet compound in a subject being treated with the compound comprising a reagent which immunoreacts with the compound. In a preferred embodiment of the kit, the reagent comprises a monoclonal antibody produced by the hybridoma designated ATCC HB-12081. In a separately preferred embodiment of the kit, the reagent comprises a monoclonal antibody produced by the hybridoma designated at the ATCC HB-12082.

The above-described invention is further illustrated in the following Examples. These Examples are not intended, nor should they be interpreted, to limit the scope of the invention which is more fully defined in the claims which follow.

EXAMPLES

Example 1

Method for Measuring Activated Clotting Times (ACT) in Heparinized Human Whole Blood This example shows how activated clotting times were measured using a Hemochron-8000. This method can be used to calculate a standardized concentration curve for various known concentrations of anti-platelet compounds. The method can also be used to measure activated clotting times for use in calculating the ACT number for the methods of the invention.

Preparation

1. Blood was drawn from a human volunteer into a syringe containing heparin. The heparin to whole blood ratio was 1:10 such that the final concentration of heparin in the syringe was 1.4 Units/ml.

2. The Hemochron-8000 was set up to run ACT using the P-215 tubes from the same manufacturer (International Technidyne).

Procedure

1. A 1 ml sample of blood was incubated with 2.5–10 $\mu$l of compound or saline for 5 min at room temperature.

2. The Hemochron was started as 400 $\mu$l of the test sample was pipetted into the P-215 tube. The tube was gently mixed and placed into the Hemochron and turned one revolution until the light on the instrument came on.

3. Step 2 was repeated for the second channel of the instrument within 30 seconds to give an average activated clotting time. The instrument detects clot formation and displays the time for each channel, as well as the average for the two.

4. When an antibody was used, it was added after the incubation of the compound with the whole blood and allowed to incubate for an additional 5 minutes before the test was started. Steps 2 and 3 were repeated as stated above.

Example 2

Figure 1:
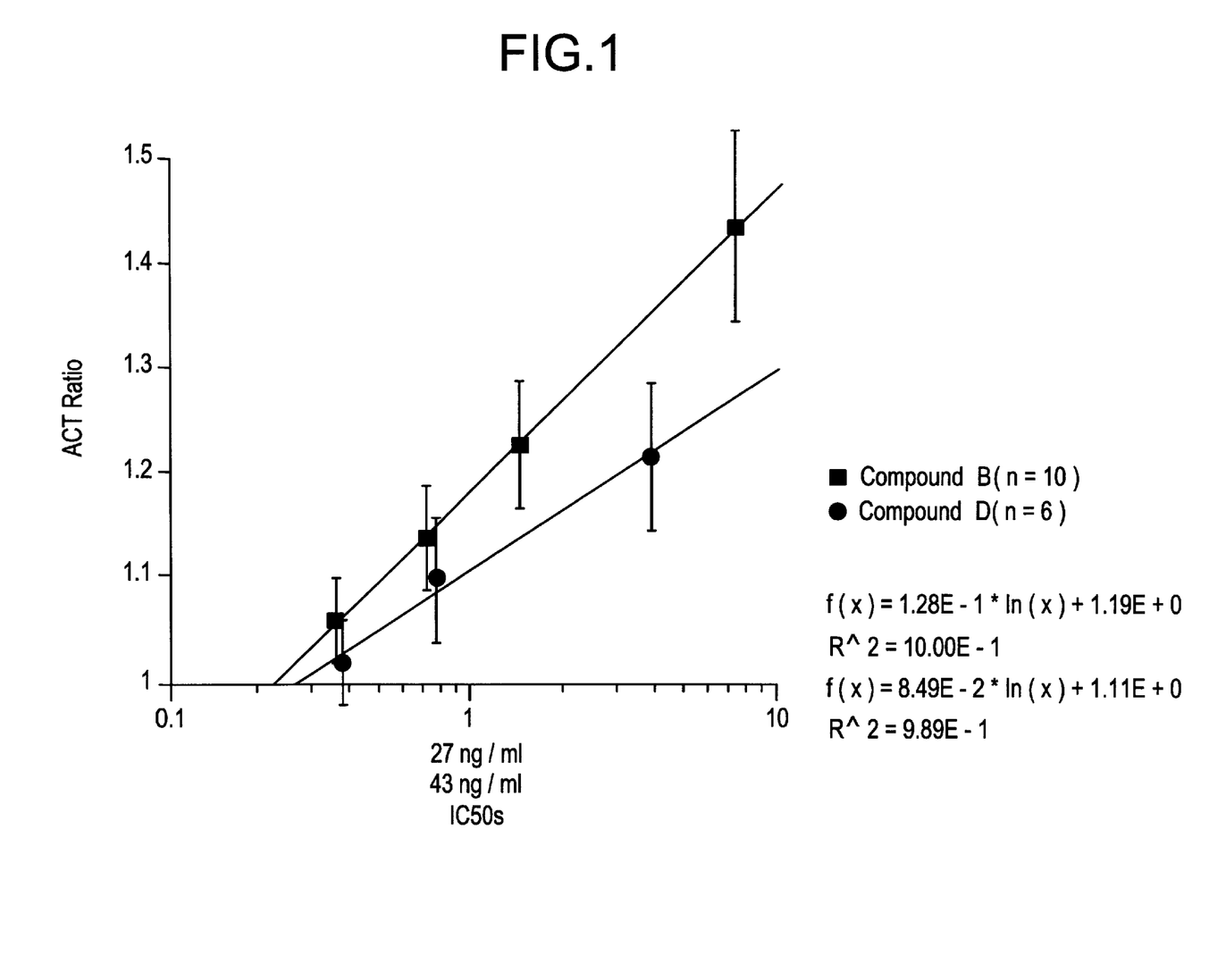
FIG. 1. This figure shows the effect on the measured activated clotting time (ACT) for various concentrations of two antiplatelet test compounds B (■) and D (●). The structures of these compounds are given in the Detailed Description of the Invention. Concentrations are represented as multiples of the 50% inhibitory concentration ($IC_{50}$) for each compound. The $IC_{50}$ of compound B is 27 ng/ml and the $IC_{50}$ compound D is 43 ng/ml.

Demonstration of Effect of Antiplatelet Compound Concentration on Activated Clotting Times The activated clotting time was first measured (in seconds) for control whole blood from each donor containing only 1.4 U/ml of heparin. The clotting times were then measured as shown in Example 1 by varying concentrations of antiplatelet compounds B&D in addition to heparin for each donor. The clotting time for a particular concentration of compound was divided by the clotting time of the control without any compound to give the clot ratio. This clot ratio is then plotted against the compound concentration. FIG. 1 shows that different concentrations of antiplatelet compounds directly effect the activated clotting time as measured by the method of Example 1.

Example 3

Determination of Effect of Polyclonal Antibodies on Activated Clotting Times

Figure 2:
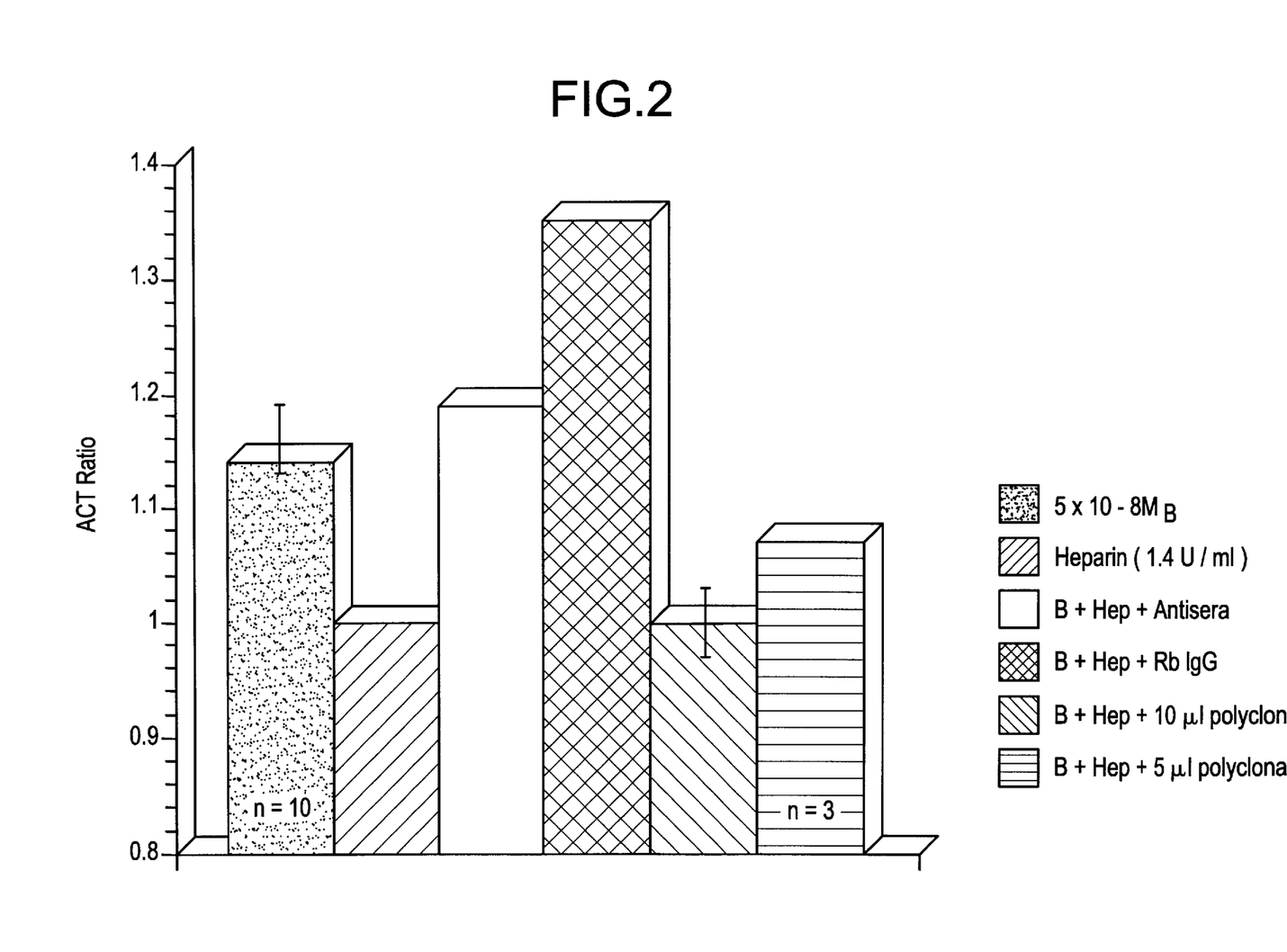
FIG. 2. This figure shows a comparison of activated clotting time ratios for blood samples with and without antibodies.

Activated clotting times were calculated as described in Example 1 for blood samples containing heparin only (control) and heparin with $5 \times 10^{-8}$ M antiplatelet compound B in the absence and presence of irrelevant rabbit antisera, rabbit IgG, and 10 $\mu$l and 5 $\mu$l of a rabbit polyclonal antibody raised to compound B. The activated clotting time ratios were calculated as described in Example 2. As can be seen in FIG. 2, the presence of antibodies had a distinct effect on the activated clotting time of blood containing the antiplatelet compound. The higher concentration of antibody (10 $\mu$l) completely reversed the effect of compound B on the clotting time.

Example 4

Monoclonal Antibody (Mab) Production

A lysine containing derivative of compound B, "compound E" (N-[N-[4-[[4-(aminoiminomethyl)phenyl]amino]-1,4-dioxobutyl]-L-aspartyl]-L-lysine,bis (trifluoroacetate), dihydrate), was used as the hapten for production of antibodies. This hapten was conjugated to thyroglobulin to provide a carrier protein and injected into mice. The mice were screened for antibodies to compound E conjugated to bovine serum albumin (BSA) and a mouse with the highest titer was chosen to produce clones for monoclonal production.

Fusions and monoclonal production were performed using standard techniques. Balb/c mice were immunized monthly via intraperitoneal injection of 25 $\mu$g of compound E. The antigen was administered in Freund's adjuvant and the course of immunizations lasted eight weeks. The spleen was excised from a mouse producing high titers of circulating anti-compound E and the spleen was dissociated to liberate splenocytes. The splenocytes were fused to mouse myeloma cells (SP2/mil6) obtained from American type Culture Collection, Rockville, Md. 20852, USA; ATCC No. CRL-2016. See, J. Immunol. Methods, Vol. 148, pp. 199–207 (1992). The cells were fused with polyethylene glycol and grown under selective conditions (HAT medium) that allow only cells resulting from the fusion of a splenocyte with a myeloma cell to proliferate. Progeny from the fusion were analyzed for the presence of antibodies by assessing the ability of conditioned media samples to bind immobilized compound E conjugated to bovine serum albumin. Positive progeny were subcloned into soft agar in order to obtain colonies of cells arising from the product of a single fusion event. Ten positive colonies were obtained which produced anti-compound E antibodies. Of the ten, nine were IgG1,K isotype and one (7C4) was IgG2,K isotype. All purified antibodies specifically bound compound B. Ascites fluid containing these antibodies were produced in Balb/c mice and the antibodies were purified to homogeneity via Protein G-SEPHAROSE® (high molecular weight substance for the separation by gel filtration of macromolecules that range in weight from about 100,000 to several million) affinity chromatography. Both the ascites and purified IgG were subsequently tested in the aggregation assay (Example 5) and ACT assay (Example 7) for neutralizing activity.

Example 5

Aggregation of Human Platelet Rich Plasma

Figure 3:
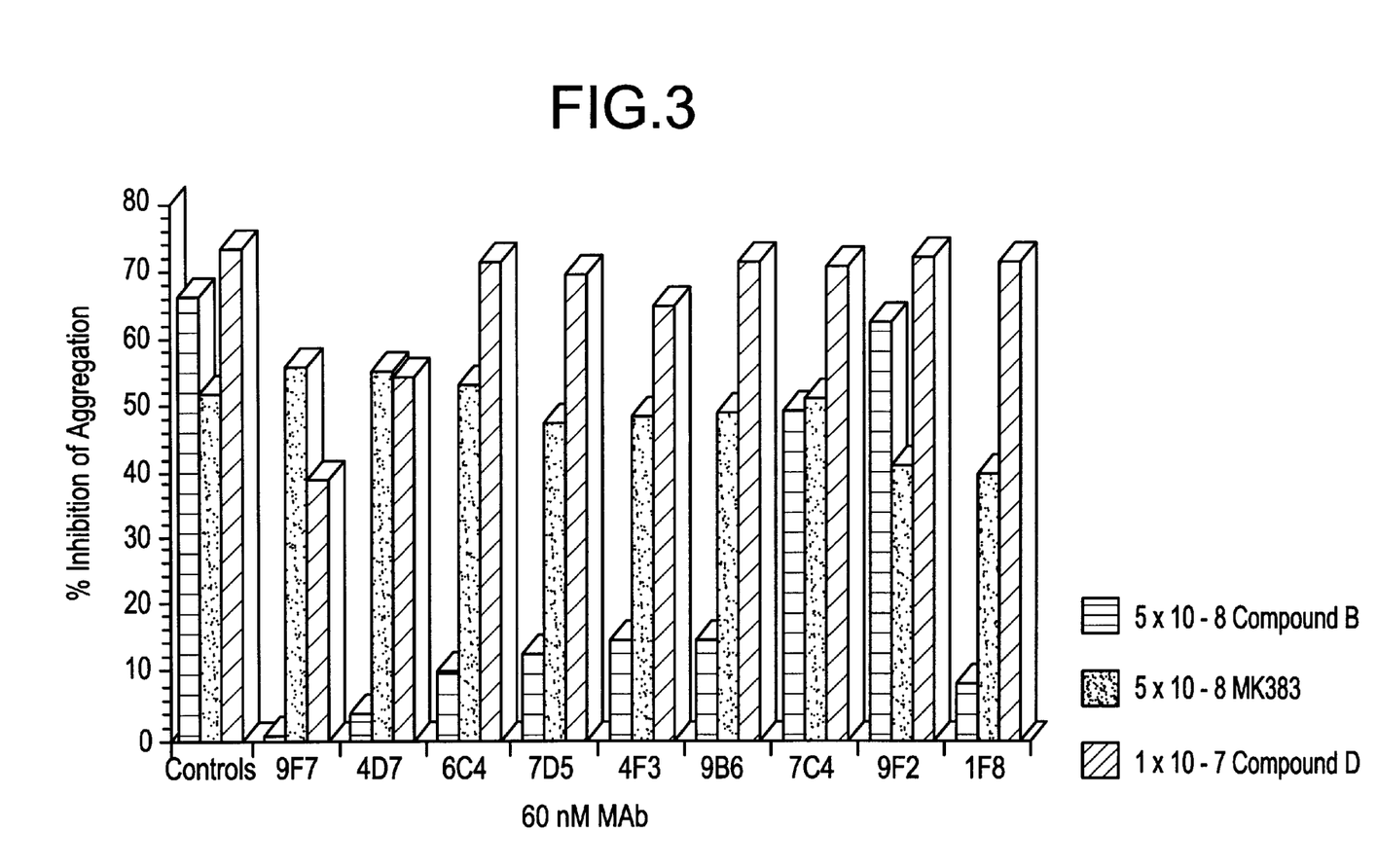
FIG. 3. Monoclonal antibodies ("Mabs") were tested in a platelet aggregation assay for their ability to recognize and neutralize antiplatelet compounds B, D and the Merck compound MK383 which was used as a negative control. The levels of antiplatelet compounds used gave at least 50% inhibition of aggregation by themselves.

Human platelet rich plasma ("PRP") was prepared by centrifugation of citrated whole blood at 970×g for 3.1 minutes at room temperature. PRP was carefully removed from red cells and placed in 50 ml conical tubes. Platelet aggregation was measured as an increase in light transmission in an aggregometer (Bio-Data model PAP-4, Horsham, Pa.) using ADP (20 $\mu$M) or collagen (4 $\mu$g/ml) as the agonist. Antibodies produced according to Example 4 were tested in aggregation for their ability to neutralize the gpIIb/IIIa antagonists compound B, compound D and Merck compound MK383 as a means of screening which ones recognized the antagonists in a useful manner. The levels of antiplatelet compounds used gave at least 50% inhibition of aggregation by themselves. Results are demonstrated in FIG. 3.

Example 6

Effect of Monoclonal Antibodies on the Activated Clotting Time of Compound B

Figure 4:
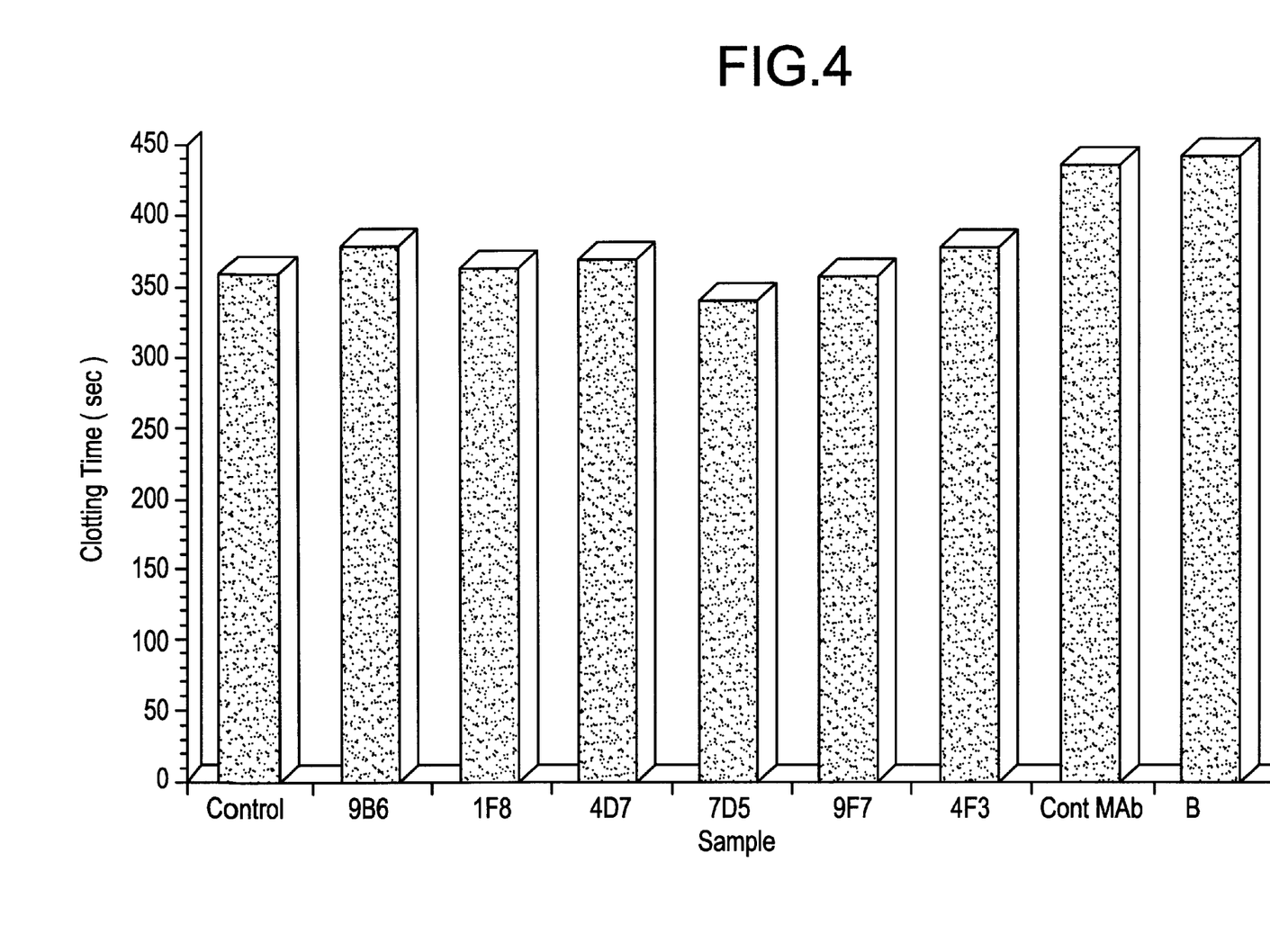
FIG. 4. This figure shows a comparison of activated clotting times for blood containing the antiplatelet compound B in the presence of various monoclonal antibodies. "Control" represents the clotting time of the blood with no compound B and no anticompound B antibody present. "Cont Mab" is the clotting time for an antibody directed against an irrelevant protein. "B" is the clotting time of blood with only compound B present.

Several monoclonal antibodies were prepared according to Example 4. Activated clotting times were calculated according to the method of Example 1 for a series of the antibodies in the presence of $5 \times 10^{-8}$ M compound B. As seen from FIG. 4, all of the monoclonal antibodies lowered the clotting time as compared to that with the compound alone. A control monoclonal antibody ("Cont Mab") against an irrelevant protein had no effect.

Example 7

Neutralizing Activity of Monoclonal Antibody

Figure 5:
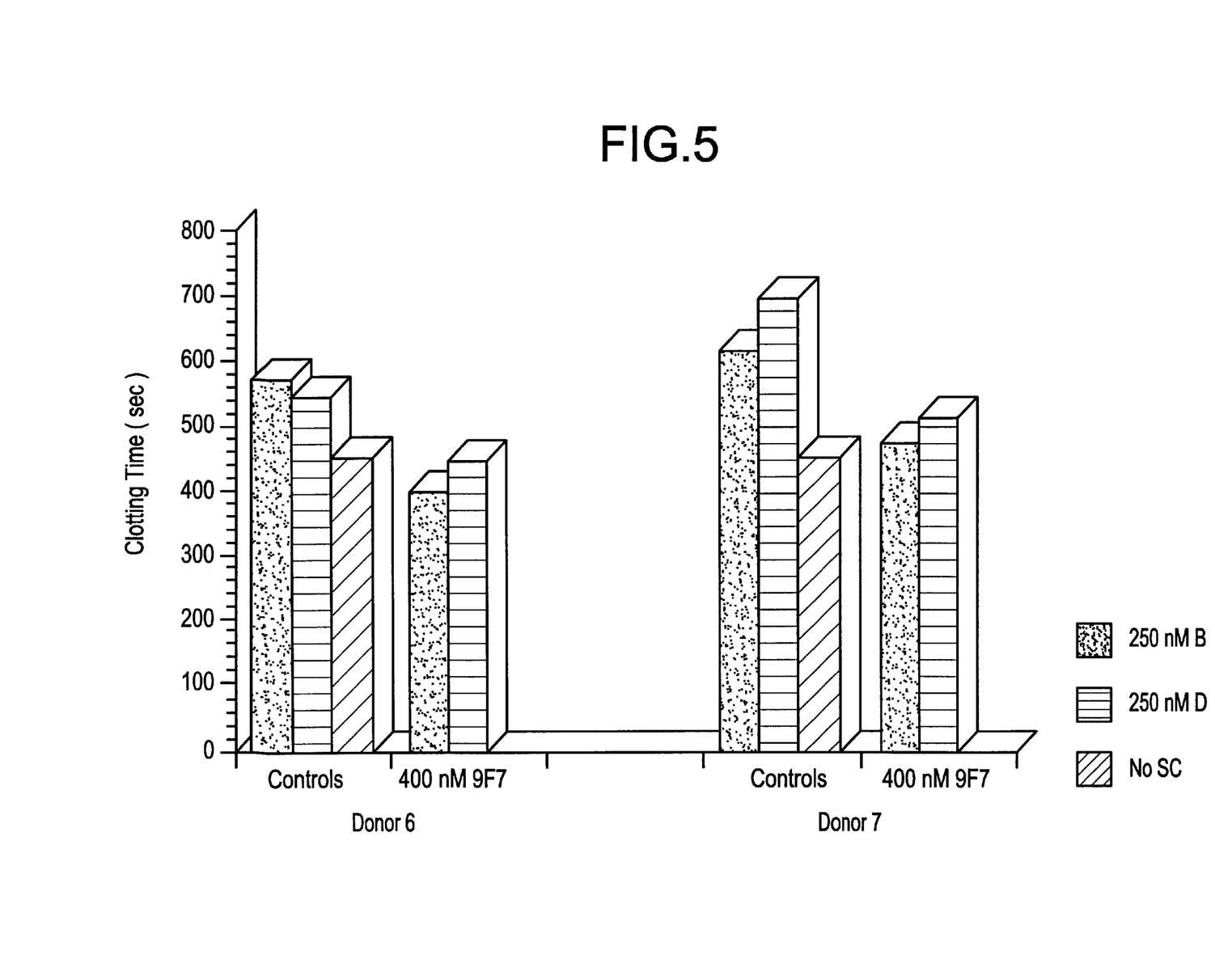
FIG. 5. Monoclonal antibody 9F7 was tested in whole blood from two different donors for its ability to neutralize antiplatelet compounds B and D.

A monoclonal antibody produced according to Example 4, and coded 9F7, was tested in whole blood from two different donors for its ability to neutralize antiplatelet compounds B and D. Activated clotting time measurements were made using a Medtronic Hemotec instrument. As seen in FIG. 5, antibody 9F7 showed a distinct effect on the measured activated clotting times for the two antiplatelet compounds.

What is claimed is:

1. A method for determining blood concentration of an antiplatelet compound in a subject being treated with the antiplatelet compound, which comprises the steps of:
   (a) taking a blood sample from the said subject;
   (b) treating the subject's blood sample with antibody combining site-containing molecules that specifically bind to said antiplatelet compound to form antibody-treated blood;
   (c) calculating activated clotting time of the subject's antibody-treated blood; and
   (d) comparing the calculated activated clotting time of the antibody-treated blood to a standardized concentration curve from normal untreated blood thereby determining the amount of the antiplatelet compound in the blood of the subject.

2. The method of claim 1 wherein the antiplatelet compound is a glycoprotein IIb/IIIa antagonist.

3. The method of claim 2 wherein the gpIIb/IIIa antagonist is chosen from the group consisting of 3S-[[4-[[4-(aminoiminomethyl)phenyl]amino]-1,4-dioxobutyl]amino]-4-pentynoic acid; and (3-[[[[1-[4-(aminoiminomethyl)phenyl]-2-oxo-pyrrolidin-3S-yl]amino]carbonyl]amino] propanoic acid, trifluoroacetate.

4. The method of claim 1 wherein the antibody combining site-containing molecules which specifically bind to the antiplatelet compound are monoclonal antibodies.

5. The method of claim 4 wherein the monoclonal antibody immunoreacts with an antiplatelet compound chosen from the group consisting of 3S-[[4-[[4-(aminoiminomethyl)phenyl]amino]-1,4-dioxobutyl]amino]-4-pentynoic acid; and 3-[[[[1-[4-(aminoiminomethyl)phenyl]-2-oxo-pyrrolidin-3S-yl]amino]carbonyl]amino] propanoic acid, trifluoroacetate.

6. The method of claim 4 wherein the monoclonal antibody is an antibody produced by a hybridoma chosen from the group consisting of the hybridomas designated ATCC HB-12081 and HB-12082.

7. A method for determining blood concentration of an antiplatelet compound in a subject being treated with the antiplatelet compound and heparin, which comprises the steps of:
   (a) taking a blood sample from the said subject;
   (b) treating the subject's blood sample with antibody combining site-containing molecules that specifically bind to said antiplatelet compound to form antibody-treated blood;
   (c) calculating activated clotting time of the subject's antibody-treated blood; and
   (d) comparing the calculated activated clotting time of the antibody-treated blood to a standardized concentration curve from normal untreated blood thereby determining the amount of the antiplatelet compound in the blood of the subject.

8. The method of claim 7 wherein the antiplatelet compound is a gpIIb/IIIa antagonist.

9. The method of claim 8 wherein the gpIIb/IIIa antagonist is chosen from the group consisting of 3S-[[4-[[4-(aminoiminomethyl)phenyl]amino]-1,4-dioxobutyl]amino]-4-pentynoic acid; and 3-[[[[1-[4-(aminoiminomethyl)phenyl]-2-oxo-pyrrolidin-3S-yl]amino]carbonyl]amino] propanoic acid, trifluoroacetate.

10. The method of claim 7 wherein the antibody combining site-containing molecules which specifically bind to the antiplatelet compound are monoclonal antibodies.

11. The method of claim 10 wherein the monoclonal antibody immunoreacts with an antiplatelet compound chosen from the group consisting of ethyl 3S-[[4-[[4-(aminoiminomethyl)phenyl]amino]-1,4-dioxobutyl]amino]-4-pentynoic acid; and 3-[[[[1-[4-(aminoiminomethyl)phenyl]-2-oxo-pyrrolidin- 3S-yl]amino]carbonyl]amino] propanoic acid, trifluoroacetate.

12. The method of claim 10 wherein the monoclonal antibody is an antibody produced by the hybridoma designated ATCC HB-12081.

13. The method of claim 10 wherein the monoclonal antibody is an antibody produced by the hybidoma designated ATCC HB-12082.

14. A method for determining blood concentration of an antiplatelet compound in a subject being treated with the antiplatelet compound, which comprises the steps of:

(a) taking a blood sample from the subject;

(b) separating the sample into at least two portions and adding antibody combining site-containing molecules that specifically bind to said antiplatelet compound to one of the portions forming antibody-treated blood;

(c) measuring the activated clotting time of at least one portion of the blood from (b) that is not treated with said antibody combining site-containing molecules;

(d) measuring the activated clotting time of at least one portion of the blood sample from (b) that is treated with said antibody combining site-containing molecules;

(e) calculating activated clotting time from the measurements of (c) and (d); and (f) comparing the calculated activated clotting time from (e) to a standardized concentration curve from normal untreated blood thereby determining the concentration of the antiplatelet compound in the subject.

15. The method of claim 14 wherein the antiplatelet compound is a gpIIb/IIIa antagonist.

16. The method of claim 15 wherein the gpIIb/IIIa antagonist is chosen from the group consisting of 3S-[[4-[[4-(aminoiminomethyl)phenyl]amino]-1,4-dioxobutyl]amino]-4-pentynoic acid; and 3-[[[[1-[4-(aminoiminomethyl)phenyl]-2-oxo-pyrrolidin-3S-yl]amino]carbonyl]amino] propanoic acid, trifluoroacetate.

17. The method of claim 14 wherein the antibody combining site-containing molecules which specifically bind to the antiplatelet compound are monoclonal antibodies.

18. The method of claim 17 wherein the monoclonal antibody immunoreacts with an antiplatelet compound chosen from the group consisting of 3S-[[4-[[4-aminoiminomethyl)phenyl]amino]-1,4-dioxobutyl]amino]-4-pentynoic acid; and 3-[[[[1-[4-aminoiminomethyl)phenyl]-2-oxo-pyrrolidin-3S-yl]amino]carbonyl]amino] propanoic acid, trifluoroacetate.

19. The method of claim 17 wherein the monoclonal antibody is an antibody produced by the hybridoma designated ATCC HB-12081.

20. The method of claim 17 wherein the monoclonal antibody is an antibody produced by the hybridoma designated ATCC HB-12082.

21. A monoclonal antibody produced by a murine hybridoma cell line, wherein the antibody immunoreacts with a glycoprotein IIb/IIIa antagonist and substantially does not immunoreact with heparin, wherein the monoclonal antibody is an antibody produced by a hybridoma cell line selected from the group consisting of the hybridomas designated ATCC HB-12081 and HB-12082.

22. The monoclonal antibody of claim 4 wherein the glycoprotein IIb/IIIa antagonist is selected from the group consisting of ethyl 3S-[[4-[[4-(aminominomethyl)phenyl] amino]-1,4-dioxobutyl]amino]-pentynoic acid; and 3[[[1-[4-(aminoiminomethyl)phenyl]-2-oxopyrrolidin-3S-yl] amino]carbonyl]amino] propanoic acid, trifluoracetate.

23. Hybridoma cell line designated ATCC HB-12081.

24. Hybridoma cell line designated ATCC HB-12082.

25. A monoclonal antibody produced by the hybridoma cell line designated ATCC HB-12081.

26. A monoclonal antibody produced by the hybridoma cell line designated ATCC HB-12082.

27. A kit for monitoring the concentration of a glycoprotein IIb/IIIa antagonist in a subject being treated with the antagonist comprising antibody combining site-containing molecules that specifically bind to said antagonist, wherein the monoclonal antibody is an antibody produced by a hybridoma cell line selected from the group consisting of the hybridomas designated ATCC HB-12081 and HB-12082.

28. The kit of claim 27 wherein the glycoprotein IIb/IIIa antagonist is selected from the group consisting of ethyl 3S-[[4-[[4-(aminominomethyl)phenyl]amino]-1,4-dioxobutyl]amino]-pentynoic acid; and 3[[[1-[4-(aminoiminomethyl)phenyl]-2-oxopyrrolidin-3S-yl]amino] carbonyl]amino] propanoic acid, trifluoracetate.

* * * * *